United States Patent [19]

Davitz

[11] 4,350,527

[45] Sep. 21, 1982

[54] GOLD-COLORED, ACID AND CORROSION RESISTANT ALLOY

[76] Inventor: Daniel Davitz, 8117 Church, Niles, Ill. 60648

[21] Appl. No.: 310,475

[22] Filed: Oct. 13, 1981

Related U.S. Application Data

[63] Continuation-in-part of Ser. No. 145,425, May 1, 1980.

[51] Int. Cl.³ .................................................. C22C 5/08
[52] U.S. Cl. ................................. 75/173 C; 75/134 C
[58] Field of Search ............. 75/173 C, 172 G, 134 C; 433/207, 222

[56] References Cited

U.S. PATENT DOCUMENTS 1,965,012  7/1934  Taylor ............................. 75/173 C
1,987,451  1/1935  Taylor ............................. 75/173 C Primary Examiner—L. Dewayne Rutledge
Assistant Examiner—David A. Hey
Attorney, Agent, or Firm—Garrettson Ellis

[57] ABSTRACT

A gold-colored, acid and corrosion resistant alloy is disclosed, usable for jewelry, dental purposes and the like. The alloy consists essentially of 15 to 20 weight percent of indium, 7 to 20 weight percent of copper, 5 to 15 weight percent of palladium, and from 0 to 10 weight percent of gold, with the balance consisting essentially of silver and optionally minor amounts of ingredients such as oxide scavengers and the like.

22 Claims, No Drawings

GOLD-COLORED, ACID AND CORROSION RESISTANT ALLOY

CROSS-REFERENCE TO RELATED INVENTION

This application is a continuation-in-part of my pending application Ser. No. 145,425, filed May 1, 1980.

BACKGROUND OF THE INVENTION

The various alloys which are used for dentistry and jewelry must be malleable, and castable at the usual temperatures in order to permit the formation of intricate shapes. Also, such alloys should provide a material which does not easily corrode, in a manner imitative of the pure noble metals.

It is of course basic that gold is one of the most valuable of metals, and is widely used in jewelry, dental inlays and the like. The look of gold is a highly valued characteristic of any metal alloy, particularly in the jewelry and dental material area.

In accordance with this invention, an alloy is provided which contains little or no gold, and yet which provides an alloy material that polishes, works, and looks like gold. Also, the alloy of this invention can be corrosion resistant in the manner of gold, even in the presence of acids such as hydrochloric acid. In the dental field, preferred alloys of this invention may be finished in the manner of regular crown and bridge gold alloys, and may be invested and casted by techniques similar to those used with known gold alloys.

The alloy of this invention may resemble 10K gold in color, for example, but also has the remarkable tendency to have a variable color depending upon its environment, being yellower in the presence of yellow walls and whiter in the presence of white walls, in a manner presenting interesting possibilities for jewelry work. Furthermore, the high corrosion resistance of preferred alloys of this invention is equal or superior to the lower karat gold alloys, even though only a little gold may be present in the alloy of this invention.

To these advantages is added the fact that the alloy of this invention may be substantially cheaper than most gold alloys, while providing the user with most of the beneficial characteristics of gold.

DESCRIPTION OF THE INVENTION

In accordance with this invention, a gold-colored, acid and corrosion resistant alloy is provided which consists essentially of the following ingredients: 15 to 20 weight percent of indium, 7 to 20 weight percent of copper, 5 to 15 weight percent of palladium, from 0 to 10 weight percent of gold, the balance consisting essentially of silver.

Preferably, the amount of silver which comprises the balance described above does not exceed 65 weight percent, and it is generally preferred for the entire alloy to include 50 or 55 to 60 percent by weight of silver.

It may also be desirable for 0.1 to 1.5 weight percent of zinc to be present to serve as an oxide scavenger. This provides a spontaneous purifying capability of the alloy, in that the zinc can react with oxygen or oxides present.

Alternatively, from 0.15 to 1 percent (and preferably no more than about 0.5 percent) of boron, calcium boride, or an equivalent boron material may be present as an oxygen scavenger or flux.

While from 15 to 20 percent of indium may be present in the alloy, it is generally preferred for 16 to 18 percent of the indium to be present. In concentrations of less than 15 percent of indium, the gold color of the alloy of this invention can be diluted so that the alloy no longer can be considered to be gold-like, but does retain many of the other desirable characteristics. Above a concentration of 20 percent indium, the alloy becomes substantially low melting, which may reduce the desirability of the material in some circumstances.

The indium tends to provide flowability to the material, and also serves as a scavenger for removing oxides in the manner similar to that previously described with respect to zinc and boron compounds. Also, as previously mentioned, the indium provides much of the remarkable reflective characteristic of the metal so that it tends to acquire the color of its environment to some extent.

It is desirable for at least 7 percent of copper to be present, the copper serving both as a coloring agent, and also serving to inhibit the tarnishing of the silver, which is preferably present in large quantities in the alloy of this invention. At concentrations in excess of 17 percent by weight copper, it has been noted that the alloy tends to tarnish when utilized as a dental structural material, for example a crown or a bridge. However, the copper concentration may suitably be up to 20 percent by weight if the use of the alloy of this invention is intended for jewelry or some other drier environment than the mouth. It is generally preferable for 10 or 12 to 15 percent of copper to be present in the alloy of this invention.

With respect to the palladium ingredient, the material appears to also act to strongly inhibit tarnishing of the alloy at concentrations of about 9 percent and more. At palladium concentrations in excess of 11 percent by weight, the gold color of the alloy of this invention begins to be diluted substantially, so the range of 9 to 11 percent is generally preferred, although useful alloys having gold color and tarnish resistance may be made outside of this range, particularly those having palladium concentrations of 5 to 15 percent by weight.

As previously stated, it is generally preferred for most of the balance of the alloy of this invention to comprise silver, to provide an alloy of this invention which looks and behaves like gold while exhibiting a greatly reduced cost.

Preferably, from more than 3 to 8 percent by weight of gold are added to the alloy of this invention, to provide significant and unexpected improvements in the tarnish and corrosion resistance of the alloy of this invention. Such alloys are even tarnish-resistant in sodium sulfide solution. At gold concentrations of 1 to 3 weight percent gold-like alloys may also be formed which exhibit acceptable tarnish resistance in a sulfide environment.

Specifically, a preferred dental alloy in accordance with this invention contains approximately 16 percent of indium, 10 percent of copper, 57.25 percent of silver, 10.25 percent of palladium, 0.5 percent zinc, and 6 percent of gold, all by weight. Such an alloy resembles 10K gold, and is acid resistant, noncorroding, easily malleable, and castable, being highly suitable for fabrication into dental bridges, crowns, and inlays.

Another preferred alloy which may be particularly used for jewelry contains approximately 18 percent of indium, 14 percent of copper, 51 percent of silver, 10.25 percent of palladium, 0.75 percent of zinc and 6 percent of gold, all by weight. This alloy also resembles 10K gold and is particularly attractive for use in jewelry.

Still another preferred alloy of lower gold content contains by weight, approximately 17 percent of indium, 13.25 percent of copper, 58 percent of silver, 10 percent of palladium, and 1.75 percent of gold.

Yet another preferred alloy contains, by weight, 17 percent of indium, 13 percent of copper, 57 percent of silver, 10 percent of palladium, 2 percent of gold, and 1 percent of zinc.

The preferred alloys of this invention described above have a casting temperature of about 1575° F. and a melting temperature of about 1490° F. Other physical properties of the materials are essentially as follows:

| | |
|---|---|
| Burn-out | 20 to 40 min. at 900° F. |
| BHN | 132 |
| Vickers | 138 |
| Elongation | 11 percent |
| Density | 9.6–9.7 g./cc. |
| Tensile strength | 66,000 psi |

The above has been offered for illustrative purposes only, and is not intended to limit the invention of this application, which is as defined in the claims below.

That which is claimed is:

1. A gold-colored, acid and corrosion-resistant alloy which consists essentially of 15 to 20 weight percent of indium, 7 to 20 weight percent of copper, 5 to 15 weight percent of palladium, and from 0 to 10 weight percent of gold, the balance consisting essentially of silver.

2. The alloy of claim 1 in which said balance does not exceed 65 weight percent of the alloy.

3. The alloy of claim 1 in which from 0.1 to 1.5 weight percent of zinc is present to seve as an oxide scavenger.

4. The alloy of claim 1 in which from 0.05 to 1 weight percent of an agent is present selected from the group consisting of boron and calcium boride.

5. The alloy of claim 4 in which no more than 0.5 percent of said agent is present.

6. The alloy of claim 1 which contains, by weight, 16 to 18 percent of indium, 12 to 15 percent of copper, and 55 to 60 percent of silver.

7. The alloy of claim 1 in which from 55 to 60 percent by weight of silver is present.

8. The alloy of claim 1 which contains 16 to 18 percent of indium.

9. The alloy of claim 1 which contains 10 to 15 weight percent of copper.

10. The alloy of claim 1 which contains from more than 3 to 8 weight percent of gold.

11. The alloy of claim 1 which contains from 1 to 3 weight percent of gold.

12. The alloy of claim 11 which contains from 9 to 11 weight percent of palladium.

13. A dental alloy for bridges, fillings, and the like which consists essentially of from 15 to 20 weight percent of indium, from 7 to 17 weight percent of copper, and from 9 to 11 weight percent of palladium, and from 1 to 8 weight percent of gold, the balance consisting essentially of silver.

14. The dental alloy of claim 13 in which from 0.1 to 15 weight percent of zinc is present to seve as an oxide scavenger.

15. The dental alloy of claim 14 in which from 0.05 to 0.5 weight percent of an agent is present selected from the group consisting of boron and calcium boride.

16. The dental alloy of claim 15 which contains, by weight, 16 to 18 percent of indium, 12 to 15 percent of copper, and 50 to 60 percent of silver.

17. A gold-colored, acid and corrosion resistant alloy which consists essentially of, by weight, 16 to 18 percent of indium, 12 to 15 percent of copper, 9 to 11 percent of palladium, 55 to 60 percent of silver, and more than 3 to 8 percent of gold.

18. The alloy of claim 17 in which from 0.1 to 1.5 weight percent of zinc is present to serve as an oxide scavenger.

19. Th alloy of claim 18 in which from 0.05 to 0.5 percent of an agent is present selected from the group consisting of boron and calcium boride.

20. A gold colored, acid and corrosion resistant alloy which consists essentially of, by weight, 16 to 18 percent of indium, 12 to 15 percent of copper, 9 to 11 percent of palladium, 55 to 60 percent of silver, and 1 to 3 percent of gold.

21. The alloy of claim 20 in which from 0.1 to 1.5 weight percent of zinc is present to serve as an oxide scavenger.

22. The alloy of claim 20 in which from 0.05 to 0.5 percent of an agent is present selected from the group consisting of boron and calcium boride.

* * * * *